(12) United States Patent
Hashmi et al.

(10) Patent No.: US 10,179,001 B2
(45) Date of Patent: Jan. 15, 2019

(54) BONE REDUCTION FORCEPS AND PLATE HOLDING FORCEPS

(71) Applicant: DePuy Synthes Products, Inc., Raynham, MA (US)

(72) Inventors: Adam Hashmi, West Chester, PA (US); David Downey, West Chester, PA (US); Eric Lui, West Chester, PA (US)

(73) Assignee: Depuy Synthes Products, Inc., Raynham, MA (US)

( * ) Notice: Subject to any disclaimer, the term of this patent is extended or adjusted under 35 U.S.C. 154(b) by 611 days.

(21) Appl. No.: 14/320,558

(22) Filed: Jun. 30, 2014

(65) Prior Publication Data
US 2015/0374425 A1 Dec. 31, 2015

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/28* | (2006.01) | |
| *A61B 17/88* | (2006.01) | |
| *A61B 17/80* | (2006.01) | |
| *A61B 17/34* | (2006.01) | |
| *A61B 17/17* | (2006.01) | |

(52) U.S. Cl.
CPC ........ *A61B 17/2833* (2013.01); *A61B 17/282* (2013.01); *A61B 17/3403* (2013.01); *A61B 17/808* (2013.01); *A61B 17/8866* (2013.01); *A61B 17/17* (2013.01); *A61B 17/1782* (2016.11); *A61B 2017/2837* (2013.01)

(58) Field of Classification Search
None
See application file for complete search history.

(56) References Cited

U.S. PATENT DOCUMENTS

| | | | |
|---|---|---|---|
| 5,674,244 A | * | 10/1997 | Mathys ..................... B25B 7/14 606/208 |
| 5,797,919 A | | 8/1998 | Brinson |
| 7,481,766 B2 | | 1/2009 | Lee et al. |
| 2005/0049629 A1 | * | 3/2005 | Koo .................... A61B 17/8866 606/201 |

(Continued)

FOREIGN PATENT DOCUMENTS

| | | |
|---|---|---|
| CH | 655646 | 5/1986 |
| CN | 1863479 | 11/2006 |

(Continued)

*Primary Examiner* — Sameh Boles
(74) *Attorney, Agent, or Firm* — Fay Kaplun & Marcin, LLP

(57) ABSTRACT

A pair of forceps includes a first arm extending from a proximal end to a distal end and a second arm extending from a proximal end to a distal end, the second arm connected to the first arm at a pivot point in combination with a first leaf spring coupled to an inner surface of the first arm at a first attachment point and curved toward the second arm and a switch coupled to an inner surface of the second arm and having a switch opening extending therethrough receiving the first leaf spring to form a ratchet mechanism maintaining a desired position of as the first and second arms relative to one another as they are radially compressed to a grasping configuration.

14 Claims, 4 Drawing Sheets

(56) References Cited

U.S. PATENT DOCUMENTS

| | | | | |
|---|---|---|---|---|
| 2006/0149315 | A1* | 7/2006 | Kebel | A61B 17/28 |
| | | | | 606/205 |
| 2009/0012539 | A1* | 1/2009 | Zohman | A61B 17/2812 |
| | | | | 606/151 |
| 2009/0254130 | A1 | 10/2009 | Wotton, III | |
| 2010/0152789 | A1 | 6/2010 | Dell'Oca | |

FOREIGN PATENT DOCUMENTS

| | | |
|---|---|---|
| DE | 102007008918 | 8/2008 |
| EP | 1415600 | 5/2004 |
| EP | 2623059 | 8/2013 |
| FR | 2657246 | 7/1991 |
| GB | 2455182 | 6/2009 |

* cited by examiner

BONE REDUCTION FORCEPS AND PLATE HOLDING FORCEPS

FIELD OF THE INVENTION

The present invention generally relates to forceps for the fixation of fractures of the hand, methods of reducing fractured bones and methods for provisionally coupling bone plates to bone.

BACKGROUND

Clamps are commonly used in bone fixation procedures to correct the alignment of bone fragments and to hold the fragments in the corrected alignment until a permanent fixation device can be applied to the bone. Typical bone reduction clamps are generally inserted to a fracture site through an incision formed adjacent to the fracture site or through multiple openings formed at a plurality of predetermined positions adjacent to the target region. Such bone clamps generally comprise sharpened bone-contacting points to facilitate non-slip grasping of the bone. However, these clamps are sometimes susceptible to sliding over the bone and may require a surgeon to manually maintain clamping pressure on the forceps for the entirety of a target procedure.

SUMMARY OF THE INVENTION

The present invention is directed to a pair of forceps, comprising a first arm extending from a proximal end to a distal end and a second arm extending from a proximal end to a distal end, the second arm connected to the first arm at a pivot point in combination with a first leaf spring coupled to an inner surface of the first arm at a first attachment point and curved toward the second arm and a switch coupled to an inner surface of the second arm and having a switch opening extending therethrough receiving the first leaf spring to form a ratchet mechanism maintaining a desired position of as the first and second arms relative to one another as they are radially compressed to a grasping configuration.

BRIEF DESCRIPTION OF THE DRAWINGS

Several embodiments of the invention will be described in the following by way of example and with reference to the accompanying drawings in which.

DETAILED DESCRIPTION

Figure 1:
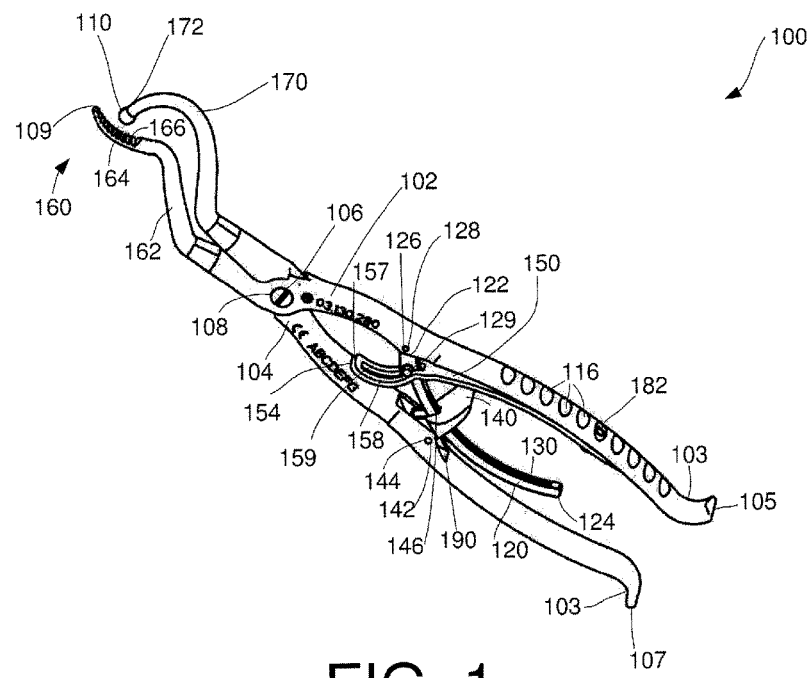
FIG. 1 shows a perspective view of plate holding forceps according to an exemplary embodiment of the invention.

The exemplary embodiments may be further understood with reference to the following description and the appended drawings, wherein like elements are referred to with the same reference numerals. A first embodiment relates to an apparatus and method for provisionally locking a bone plate in a desired position over a bone. More specifically, the exemplary plate holding forceps include first and second arms pivotally attached to one another and movable between an expanded configuration in which first and second distal ends thereof are separated from one another by a first distance and a compressive configuration in which the first and second distal ends are brought toward one another to grasp a bone and bone plate therebetween. A proximal portion of the first arm includes first and second leaf springs which maintain the forceps in the expanded configuration until a compressive force is applied thereto. The second leaf spring is slidably received through a switch formed on a proximal portion of the second arm with a ratcheting engagement. The first distal end of the first arm includes a curved portion formed to extend over a portion of an outer periphery of a bone opposing a location of a bone plate. The second distal end includes a ball tip formed to be received through a plate hole extending through the bone plate. In an operative configuration, as the first and second arms are compressed, the second leaf spring slides proximally into an opening extending through the switch. The second leaf spring includes a plurality of angled ratcheting walls formed to prevent the second leaf spring from moving distally out of the switch. Thus, as the first and second arms are compressed, the ratcheting mechanism maintains frictional engagement on a bone and bone plate positioned between first and second distal ends without the need for consistent compression by the surgeon. In a second embodiment, bone reduction forceps are provided with substantially the same ratcheting mechanism as the plate holding forceps. The bone reduction forceps include, at a first distal end, a curved section formed to engage an outer surface of a bone and, at a second distal end, a drill guide cannula configured to guide a drilling device therethrough and into the bone. In accordance with an exemplary method of the second embodiment, fragments of a fractured bone are brought into a provisional alignment. The bone reduction forceps are positioned over the bone and compressed with ratchet action maintaining the forceps and, consequently, the fragments in the desired orientation even after the forceps are released by the surgeon. The drilling device is then inserted through the cannula to form a bone hole in a desired position through the bone. A guidewire, bone screw or bone pin may then be inserted through the hole to secure the fragments to one another. As used herein, the term proximal refers to a direction approaching a surgeon or other user in an operative configuration and the term distal refers to a direction approaching a target bone of the patient in the operative configuration.

As shown in FIGS. 1-4, bone plate holding forceps 100 according to a first exemplary embodiment of the present invention comprises first and second arms 102, 104 extending from proximal ends 105, 107, respectively, to distal ends 109, 110. The arms are pivotally joined to one another at a pivot point 106 by, for example, a set screw 108. Proximal ends 105, 107 of the first and second arms 102, 104, respectively, comprise finger loops 103 that are flared radially outward to aid in gripping thereof, as those skilled in the art will understand. Proximal portions 112, 114 of the first and second arms 102, 104, respectively, located proximally of the pivot point 106 are surface treated to further aid in gripping thereof. In one embodiment, the surface treatment may include a plurality of recesses 116 etched into the first and second proximal portions 112, 114. The recesses 116 may be arranged orthogonal to a longitudinal axis 118 of the first and second proximal portions 112, 114. It is noted, however, that the recesses 116 may extend at any angle relative to the axis 118 without deviating from the scope of the invention. The first and second proximal portions 112, 114 follow a curved convex path from the pivot point 106 to the proximal ends 105, 107.

The first arm 102 further comprises a first leaf spring 120 extending from a first end 122 coupled to an inner surface of the first arm 102 to a second free end 124. The first end 122 of the first leaf spring 120 includes an opening (not shown) receiving a first locking pin 126 therethrough. Specifically, a first arm pin opening 128 is formed in the first arm 102 to receive the first locking pin 126. The first locking pin 126 extends through the first arm pin opening 128, into the opening extending through the first end 122 of the first leaf spring 120 to lock the first leaf spring 120 to the first arm 102. The first leaf spring 120 further comprises a protrusion 129 extending laterally therefrom to slidably engage a second leaf spring 150 also coupled to the first arm 102, as will be described in greater detail later on.

Figure 4:
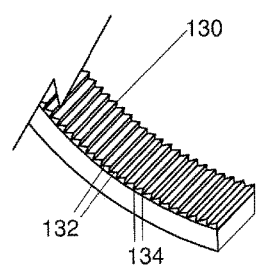
FIG. 4 shows a partial zoom view of a first leaf spring of the plate holding forceps of FIG. 1.

A first side wall of the first leaf spring 120 includes a plurality of ratcheting surfaces 130, which, in an operative configuration, engage a switch 140 forming a ratchet. The ratcheting surfaces 130 include a plurality of first walls 132 angled away from the body of the first leaf spring 120 and a plurality of second walls 134 extending substantially orthogonally relative to the first leaf spring 120, as shown in FIG. 4.

The second leaf spring 150 extends from a first end 152 coupled to an inner surface of the first arm 102 to a free end 154. A locking screw 180 is inserted through an opening (not shown) extending through the second leaf spring 150 and into an opening 182 extending through the first arm 102. In another embodiment, the locking screw 180 may be a rivet, pin or other locking mechanism. As those skilled in the art will understand, the locking screw 180 may be removed from the forceps 100 to permit dismantling and subsequent sterilization thereof. The second leaf spring 150 includes a first portion 156 curved toward the first arm 102 and a second portion 158 curved toward the second arm 104. As would be understood by those skilled in the art, a length of the second portion 158 is selected to achieve a desired range of movement of the first and second arms 102, 104, respectively, relative to one another. The second portion 158 further comprises an elongated opening 159 extending therethrough in alignment with a longitudinal axis of the second leaf spring 150. In an operative configuration, the first leaf spring 120 extends through the opening 159 with the protrusion 129 engaging a wall surrounding the opening 159 providing a limit to the range of motion of the first leaf spring 120 through the second leaf spring 150. When the first leaf spring 120 is fully inserted into the opening 159, as shown in FIG. 1, movement of the first and second arms 102, 104 toward one another causes the protrusion 129 to slide distally along the opening 159 until engagement of the protrusion 129 with an end 157 of the opening 159 prevents further compression of the first and second arms 102, 104.

Figure 2:
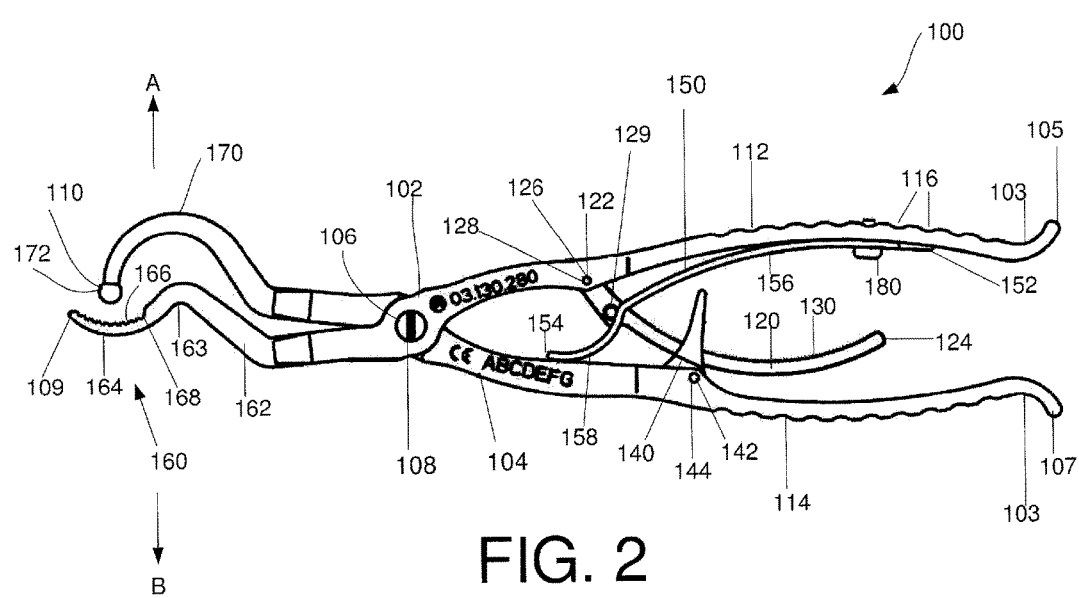
FIG. 2 shows a first side view of the plate holding forceps of FIG. 1.
Figure 3:
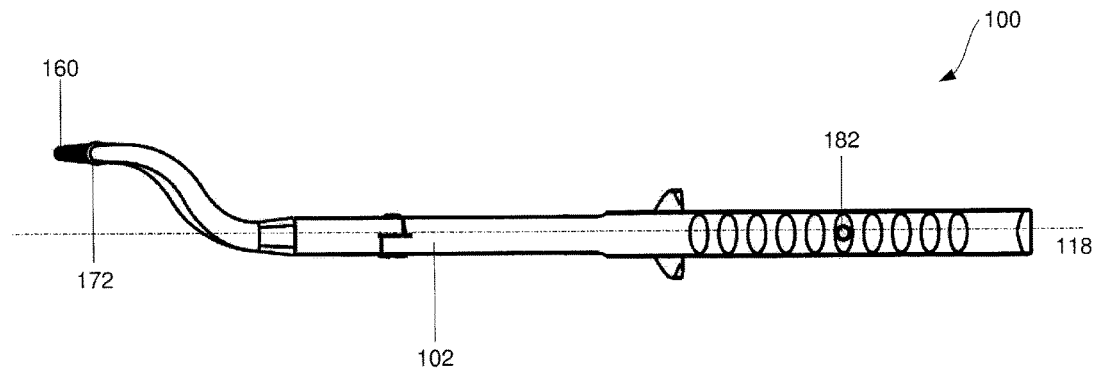
FIG. 3 shows a second side view of the plate holding forceps of FIG. 1.

Movement of the first and second arms 102, 104, respectively, is further restricted by the switch 140 disposed on an inner surface of the second arm 104 and oriented toward the first arm 102. The switch 140 includes an opening (not shown) extending therethrough and configured to align with an opening 142 extending through the second arm 104. A pin 144 extends through the opening 142 and the opening (not shown) of the switch 140. The switch 140 is rotatable about the pin 144 from a first position seated flush against the second arm 104 to a second position oriented toward the first arm 102, as shown in FIG. 2. Specifically, an inner surface of the second arm 104 includes a recess 190 formed to seat the switch 140 therein in the first position. The switch 140 includes an opening 146 extending therethrough and oriented to receive the first leaf spring 120 therethrough, maintaining the switch 140 in the second position. The opening 146 is configured to engage the ratcheting surface 130 of the first leaf spring 120 as the first and second arms 102, 104 are radially compressed to maintain a desired relative position of the first and second arms 102, 104. Specifically, a first wall (not shown) of the opening 146 is formed with an angled wall oriented to permit the first wall 132 to slide therepast and lockingly engage the second wall 134. As those skilled in the art will understand, this configuration prevents the forceps 100 from opening after being brought into a closed configuration. Thus, the forceps 100 are maintained in the locked configuration until a target procedure has been completed. The switch 140 is then pulled back to allow the forceps to unlock and open. In accordance with an exemplary method, as will be described in greater detail later on, the forceps 100 may be moved between locked and unlocked configurations any number of times in accordance with the requirement of a target procedure.

The distal end 109 of the first arm 102 includes a curved bone engaging portion 160 shaped to straddle an outer surface of a bone. Specifically, a distal length of the first arm 102 includes an angled wall 162 curved toward a direction A and a curved portion 164 extending distally therefrom toward a direction B, the angled wall 162 being connected to the curved portion 164 at a vertex 163. A curvature along an outer wall of the vertex 163 is selected, for example, to form a clearance for a tendon when the forceps 100 is positioned over a bone. A bone-contacting surface of the curved portion 164 includes one or more serrations 166 formed to facilitate grasping of the bone. The serrations 166 may be provided on a recessed portion 168 defining a reduced thickness of the curved portion 164. In one embodiment, the serrations 166 are formed as a plurality of elongated cutouts extending orthogonal to the longitudinal axis 118 of the forceps 100. In another embodiment, the cutouts extend at any suitable angle relative to the axis 118. In yet another embodiment, the serrations 166 may be formed as a plurality of spikes oriented to engage the bone in the operative configuration. In yet another embodiment, the curved portion 164 may be non-serrated. The recessed portion 168 provides a seating surface for the bone while the curved portion 164 cradles around the bone. A length and curvature of the curved portion 166 is selected to permit grasping of a metacarpal bone, as will be described in greater detail with respect to the exemplary method. Specifically, a curvature of the curved portion 166 is selected to substantially match a curvature of an outer surface of a target metacarpal bone. The curvature of the curved portion 166 in an exemplary embodiment is 9 mm which was found to most closely match the curvature of a target portion of bone (e.g., target portions of phalange bones). Alternatively, can the curved surface 164 be formed with a non-circular curvature—e.g., elliptical—or may even be made flat. In another embodiment, the curved portion 166 is made substantially straight, extending along an axis parallel to the longitudinal axis 118. In another embodiment, the distal end 109 may be substantially blunt and in a further embodiment, the distal end 109 is sharpened to aid in insertion thereof through soft tissue to a target site.

The distal end 110 of the second arm 104 includes a curved body 170 which curves away from the distal end 109 in the direction A. A curvature of the body 170 is selected so that an increased diameter ball tip 172 at the distal end 110 is positioned adjacent the curved portion 166 in a closed configuration. Specifically, the curved body 170 is curved along an axis of curvature selected so that only the ball tip 172 contacts a bone plate in an operative configuration while proximal portions of the body 170 are angled away from and therefore do not impede visualization of the bone plate. The ball tip 172 is sized to be received through a bone plate hole (not shown) of a bone plate (not shown). Specifically, the ball tip 172 may be at least partially received through the bone plate hole while the serrated surface 166 contacts a portion of a bone on an opposing side of a bone to maintain a position of the bone plate over the bone. In another embodiment, the ball tip 172 includes a spike (not shown) formed on a bone-facing side thereof to aid in grasping the bone. In yet another embodiment, the tip 172 is conical, terminating in one of a blunted and a sharpened tip.

As shown in the side view of FIG. 2, distal lengths of the first and second arms 102, 104, respectively, are curved so that distal ends 109, 110 are seated within a plane laterally offset from a plane housing proximal portions of the first and second arms 102, 104. This configuration permits a surgeon or other user to manipulate the forceps 100 without obstructing their field of vision to a target treatment area. Widths of the distal lengths of the first and second arms 102, 104, respectively (i.e., distal of the set screw 108) are substantially uniform. In another embodiment, a width of the distal portion of the first arm 102 is increased to aid in the gripping of the bone in the operative configuration.

In accordance with an exemplary method according to the invention, the forceps 100 are assembled such that the first leaf spring 120 is at least partly received within the opening 146 of the switch 140. In a preferred embodiment, the first leaf spring 120 is inserted such that at least one first angled wall 132 is lockingly received within the opening 146. In this configuration, distal ends 109, 110, respectively, are radially separated from one another by a distance at least greater than a combined width of a bone and bone plate to be grasped. The bone plate (not shown) is then positioned in a target position over the bone and the forceps 100 are positioned such that the ball tip 172 is received within a bone plate hole of the bone plate. A manual compression force is then applied to the finger loops 103 moving the first leaf spring 120 proximally into the opening 146 of the switch 140 and moving the first and second distal ends 109, 110, respectively, to move toward one another. As the forceps 100 are compressed, the surgeon may align the serrated surface 166 to ensure seating thereof over a target portion of bone opposing a bone surface having the bone plate mounted thereover. The forceps 100 are compressed until the ball tip 172 and bone engaging portion 160 are compressively received over the bone and bone plate with a pressure sufficient to maintain a position of the bone plate over the bone. The ratchet maintains the forceps 100 in place over the bone and bone plate after the surgeon releases the forceps, freeing the surgeon's hands to facilitate the target bone fixation procedure. One or more bone fixation elements (e.g., bone screws, bone pins, etc.) may then be inserted through the bone plate and into the bone. The forceps 100 may then be removed from the bone plate and bone. Optionally, an additional bone fixation element may be inserted through the bone plate hole previously housing the ball tip 172.

It is noted that although the exemplary method is directed to a positioning of the curved portion 164 directly over a bone, the method is also intended to cover an embodiment wherein the curved portion 164 is placed outside the skin. Specifically, in this embodiment the ball tip 172 may be inserted through a plate hole while the curved portion 164 remains outside of the body and rests over the skin located opposite the bone plate site.

Figure 5:
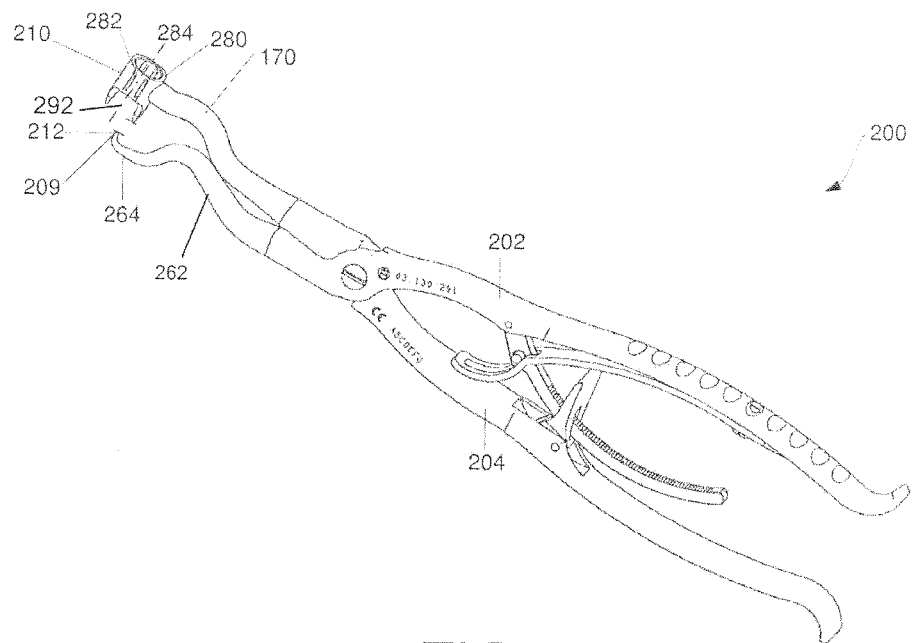
FIG. 5 shows a perspective view of a bone reduction forceps according to a second embodiment of the invention.
Figure 6:
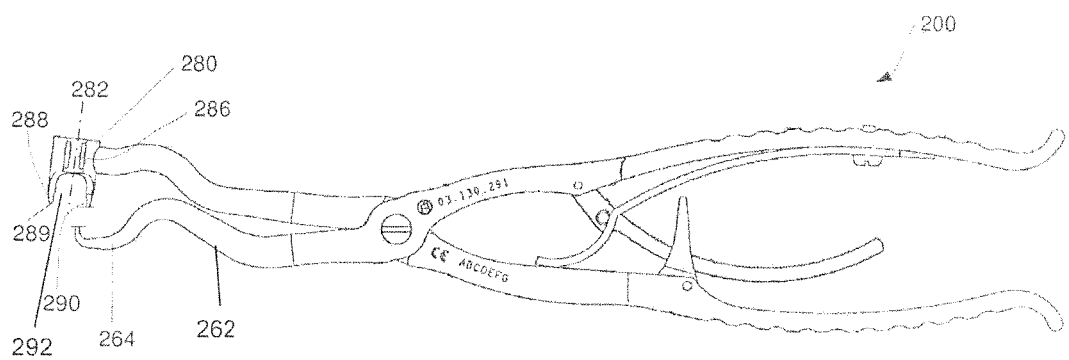
FIG. 6 shows a first side view of the bone reduction forceps of FIG. 5.
Figure 7:
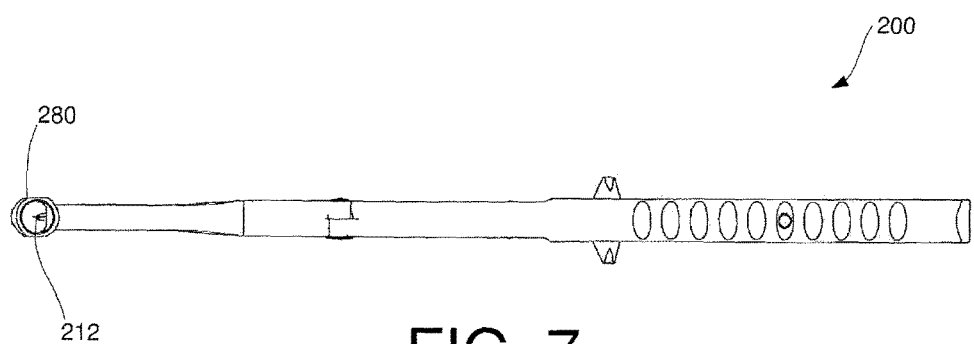
FIG. 7 shows a second side view of the bone reduction forceps of FIG. 5.

FIGS. 5-7 depict forceps 200 according to another embodiment of the invention. Whereas the forceps 100 are plate holding forceps, the forceps 200 are reduction forceps, as will be described in greater detail hereinafter. The forceps 200 are substantially similar to the forceps 100 except as noted below, wherein like elements have been referenced with like reference numerals. The forceps 200 vary from the forceps 100 in the configuration of distal ends 209, 210. The first distal end 209 of a first arm 202 includes an angled wall 262 and curved portion 264 formed substantially similar to the angled wall 162 and the curved portion 164 of the forceps 100. The first distal end 209 terminates in a pointed tip 212 formed to contact a bone in an operative configuration. Similar to the curved surface 164, the curved surface 264 is also curved to correspond to a curvature of a bone. However, whereas the curved surface 164 is formed to engage the bone in an operative configuration, only the tip 212 of the forceps is in direct contact with the bone.

The second distal end 210 includes the curved body 170 and a cylindrical element 280 mounted thereon. The element 280 is formed as a cylindrical tube having a channel 282 extending therethrough along a channel axis 284 oriented to extend orthogonal to the longitudinal axis 118 when the first and second arms 202, 204 are brought together to a gripping configuration. The element 280 extends from a first end 286 having a circular cross-section to a second end 288 having first and second substantially sharpened bone-contacting tips 289, 290. Specifically, the second end 288 may have two cutouts 292 extending therethrough defining the first and second bone contacting tips 289, 290. In an operative configuration, a drilling instrument may be inserted through the channel 282 to pre-drill a borehole for a bone fixation element (e.g., bone screw, bone pin, etc.).

In accordance with an exemplary method according to the invention, a fragmented or otherwise damaged bone is brought into a corrected alignment. The forceps 200 are then manipulated so that distal ends 209, 210 are positioned against opposing fragments of the bone. The first and second arms 202, 204 are compressed over the bone until a pressure applied to the bone is sufficient to temporarily maintain the bone in the corrected alignment. A drilling tip of a drilling instrument may then be inserted through the channel 282 to drill a bore through the first and second fragments. The drilled bore may be sized to receive one of a Kirschner-wire and a bone screw therethrough. The Kirschner-wire or bone screw may be inserted through the drilled bore prior to or after removal of the forceps 200 from the bone.

It will be appreciated by those skilled in the art that various modifications and alterations of the disclosed embodiments may be made without departing from the broad scope of the invention. Some of these have been discussed above and others will be apparent to those skilled in the art.

What is claimed is:

1. A pair of forceps, comprising:
   a first arm extending from a proximal end to a distal end including a curved wall formed to correspond to a contour of an outer surface of a bone;
   a second arm extending from a proximal end to a distal end, the second arm connected to the first arm at a pivot point, the distal end of the second arm including an increased diameter tip, a distal portion of the second arm including an axis of curvature selected so that only the increased diameter tip contacts a bone plate in an operative configuration;

a first leaf spring coupled to an inner surface of the first arm at a first attachment point and curved toward the second arm, the first leaf spring having a length such that a distal portion of the first leaf spring abuts the second arm to limit the range of movement of the first and second arms; and a switch coupled to an inner surface of the second arm and having a switch opening extending therethrough configured to receive a second leaf spring to form a ratchet mechanism maintaining a desired position of the first and second arms relative to one another as they are radially compressed to a grasping configuration.

2. The forceps of claim 1, wherein a side wall of the first leaf spring includes a plurality of angled walls engaging the switch opening to form the ratchet mechanism.

3. The forceps of claim 1, further comprising:
an abutment on a lateral wall of the first leaf spring; and
an elongated slot extending through the second leaf spring, the slot being sized to receive the first leaf spring therethrough, a width of the first leaf spring at the abutment being greater than a width of the elongated slot to limit movement of the first leaf spring relative to the second leaf spring.

4. The forceps of claim 1, wherein the first attachment point is positioned distally of the second attachment point.

5. The forceps of claim 1, wherein the switch is movable between a collapsed configuration and an expanded configuration in which the switch is oriented toward the first arm.

6. The forceps of claim 1, wherein a bone-contacting surface of the curved wall includes a friction-enhancing surface treatment.

7. The forceps of claim 1, wherein the distal end of the second arm includes a ball tip sized to be received in a plate hole extending through a bone plate when the distal end of the first arm is positioned over an outer surface of the bone opposite a surface over which the bone plate is positioned.

8. The forceps of claim 1, further comprising a second leaf spring coupled to the inner surface of the first arm at a second attachment point.

9. A pair of forceps, comprising:
a first arm having a distal end including a curved wall formed to correspond to a contour of an outer surface of a bone;
a second arm movably connected to the first arm, a distal end of the second arm including an increased diameter tip, a distal portion of the second arm including an axis of curvature selected so that only the increased diameter tip contacts a bone plate in an operative configuration;
a first leaf spring coupled to an inner surface of the first arm at a first attachment point and curved toward the second arm;
a second leaf spring coupled to the inner surface of the first arm at a second attachment point and curved toward the second arm, the second leaf spring having a length such that a distal end of the second leaf spring abuts the second arm to limit the range of movement of the first and second arms; and
a switch coupled to an inner surface of the second arm and having a switch opening extending therethrough receiving the first leaf spring therethrough to form a ratchet maintaining a position of the first and second arms as they are radially compressed to a grasping configuration.

10. The forceps of claim 9, wherein the first and second leaf spring bias the forceps toward a radially expanded configuration in which distal ends of the first and second arms are separated from one another by a first distance.

11. The forceps of claim 9, wherein the first attachment point is located distally of the second attachment point.

12. The forceps of claim 9, wherein a bone-contacting surface of the curved wall includes a friction-enhancing surface treatment.

13. The forceps of claim 9, wherein a distal end of the second arm includes a ball tip sized to be received in a plate hole extending through a bone plate when the distal end of the first arm is positioned over an outer surface of the bone opposite a surface over which the bone plate is positioned.

14. A pair of forceps, comprising:
a first arm extending from a proximal end to a distal end including a curved wall formed to correspond to a contour of an outer surface of a bone;
a second arm extending from a proximal end to a distal end, the second arm connected to the first arm at a pivot point, the distal end of the second arm including an increased diameter tip, a distal portion of the second arm including an axis of curvature selected so that only the increased diameter tip contacts a bone plate in an operative configuration;
a first leaf spring coupled to an inner surface of the first arm at a first attachment point and curved toward the second arm, the first leaf spring having a length such that a distal end of the first leaf spring abuts the second arm to limit the range of movement of the first and second arms;
an elongated slot extending through the first leaf spring, the slot being sized to receive a second leaf spring therethrough, the slot limiting compression of the first and second arms; and
a switch coupled to an inner surface of the second arm and having a switch opening extending therethrough configured to receive a second leaf spring to form a ratchet mechanism maintaining a desired position of the first and second arms relative to one another as they are radially compressed to a grasping configuration.

* * * * *